(12) United States Patent
Tsukada et al.

(10) Patent No.: US 10,888,685 B2
(45) Date of Patent: Jan. 12, 2021

(54) UNIT FOR BALLOON CATHETER, AND INDWELLING URETHRAL BALLOON CATHETER

(71) Applicant: TSUKADA MEDICAL RESEARCH CO., LTD., Tokyo (JP)

(72) Inventors: Osamu Tsukada, Nagano (JP); Masato Shimizu, Nagano (JP)

(73) Assignee: TSUKADA MEDICAL RESEARCH CO., LTD., Tokyo (JP)

( * ) Notice: Subject to any disclaimer, the term of this patent is extended or adjusted under 35 U.S.C. 154(b) by 655 days.

(21) Appl. No.: 15/555,264

(22) PCT Filed: Mar. 6, 2015

(86) PCT No.: PCT/JP2015/056601
§ 371 (c)(1),
(2) Date: Sep. 1, 2017

(87) PCT Pub. No.: WO2016/139814
PCT Pub. Date: Sep. 9, 2016

(65) Prior Publication Data
US 2018/0015250 A1 Jan. 18, 2018

(30) Foreign Application Priority Data
Mar. 3, 2015 (JP) .................................. 2015-041397

(51) Int. Cl.
*A61M 25/00* (2006.01)
*A61M 25/10* (2013.01)

(52) U.S. Cl.
CPC .... *A61M 25/0017* (2013.01); *A61M 25/1018* (2013.01); *A61M 25/1025* (2013.01);
(Continued)

(58) Field of Classification Search
CPC .......... A61M 25/1018; A61M 25/0017; A61M 25/1025; A61M 25/002; A61M 2025/0046; A61M 2205/0205
See application file for complete search history.

(56) References Cited

U.S. PATENT DOCUMENTS

| | | | | |
|---|---|---|---|---|
| 3,742,959 A | * | 7/1973 | Patel ..................... | A61M 25/00 604/102.01 |
| 4,207,899 A | * | 6/1980 | Patel ................. | A61M 25/1025 604/100.01 |

(Continued)

FOREIGN PATENT DOCUMENTS

| | | |
|---|---|---|
| JP | S6253673 A | 3/1987 |
| JP | S63117768 A | 5/1988 |

(Continued)

OTHER PUBLICATIONS

International Search Report (in English and Japanese) and Written Opinion of the International Searching Authority (in Japanese) issued in PCT/JP2015/056601, dated Jun. 9, 2015; ISA/JP.

(Continued)

*Primary Examiner* — Tatyana Zalukaeva
*Assistant Examiner* — Jessica R Arble
(74) *Attorney, Agent, or Firm* — Harness, Dickey & Pierce, P.L.C.

(57) ABSTRACT

A purpose is to enable partial replacement of an indwelling urethral catheter. A unit for a balloon catheter according to the present invention includes a urethral catheter tube (13) provided with a first urethral catheterization passage (14), a branch tube (11) provided with a first passage (12) adapted to allow passage of a liquid used to inflate or deflate a balloon (54), and a connecting tube (30) configured to be connected at one end to the first urethral catheterization passage (14) or the first passage (12).

6 Claims, 3 Drawing Sheets

(52) U.S. Cl.
CPC ... *A61M 25/002* (2013.01); *A61M 2025/0046* (2013.01); *A61M 2205/0205* (2013.01)

(56) References Cited

U.S. PATENT DOCUMENTS

| | | | |
|---|---|---|---|
| 4,222,384 A * | 9/1980 | Birtwell | A61M 25/1025 |
| | | | 604/103 |
| 4,335,723 A * | 6/1982 | Patel | A61L 29/041 |
| | | | 604/97.02 |
| 4,732,139 A | 3/1988 | Kawashima et al. | |
| 2006/0111691 A1 | 5/2006 | Bolmsjo et al. | |
| 2008/0051762 A1 | 2/2008 | Tsukada et al. | |
| 2011/0160706 A1 * | 6/2011 | Behan | A61M 39/0606 |
| | | | 604/544 |

FOREIGN PATENT DOCUMENTS

| | | |
|---|---|---|
| JP | H06-3347 U | 1/1994 |
| JP | 2009-511114 A | 3/2009 |
| JP | 2011-250903 A | 12/2011 |
| JP | 2013-118915 A | 6/2013 |
| WO | WO 93/25261 A1 | 12/1993 |
| WO | WO-2005-018714 A1 | 3/2005 |

OTHER PUBLICATIONS

Extended European Search Report dated Oct. 26, 2018 in corresponding European Application No. EP15883981.1.

* cited by examiner ized to the present embodiment.
UNIT FOR BALLOON CATHETER, AND INDWELLING URETHRAL BALLOON CATHETER

CROSS REFERENCE TO RELATED APPLICATIONS

This application is a U.S. National Phase Application under 35 U.S.C. 371 of International Application No. PCT/JP2015/056601 filed on Mar. 6, 2015 and published in Japanese as WO 2016/139814 on Sep. 9, 2016. This application is based on and claims the benefit of priority from Japanese Patent Application No. 2015-041397 filed Mar. 3, 2015. The entire disclosures of all of the above applications are incorporated herein by reference.

TECHNICAL FIELD

The present invention relates to a unit for a balloon catheter and to an indwelling urethral balloon catheter.

BACKGROUND ART

As a conventional catheter for the purpose of urinary management, a so-called balloon catheter with a balloon attached to a distal end is known. When the balloon catheter is inserted into the urethra, the balloon is deflated. Also, when the balloon catheter is placed in the bladder, the balloon is inflated by injecting sterile water into the balloon from a rear end of the balloon catheter. This prevents a distal end of the balloon catheter from falling off the bladder. When used for a long time, the balloon catheter may cause urinary tract infection and behavior of the user may be restricted as well.

Thus, a Nelaton catheter has been developed which can prevent urinary tract infection and guarantee the user some freedom of movement. Because no balloon is attached to the distal end, the Nelaton catheter cannot be kept placed in the urethra for a long time. The user always carries the Nelaton catheter in a case filled with an antiseptic solution. The user takes the Nelaton catheter out of the case as needed, and inserts the catheter into the bladder through the urethra by himself/herself to discharge urine.

Typically, the Nelaton catheters are disposable, making it necessary to constantly carry as many Nelaton catheters as needed, which is inconvenient. Also, the disposable Nelaton catheters have a problem of large disposal quantities. Thus, an intermittent/indwelling urethral catheter set is known which combines an indwelling function of conventional balloon catheters and a self-urethral catheterization function of conventional balloonless catheters (Nelaton catheters) (see, for example, PTL 1).

CITATION LIST

Patent Literature

PTL 1: International Publication WO 2005/018714

SUMMARY OF INVENTION

Technical Problem

The intermittent/indwelling urethral catheter set described in PTL 1 can be used multiple times through sterilization, and thus can reduce the disposal quantities compared to the disposable Nelaton catheter. On the other hand, the intermittent/indwelling urethral catheter set is discarded after being used for a predetermined period.

To reduce running costs of the intermittent/indwelling urethral catheter set, preferably only a necessary part of the intermittent/indwelling urethral catheter set is replaceable. However, the intermittent/indwelling urethral catheter set described in PTL 1 does not assume partial replacement.

The present invention has been made in view of the above problem and has an object to enable partial replacement of an indwelling urethral catheter.

Solution to Problem

One aspect of a unit for a balloon catheter according to the present invention comprises: a balloon catheter duct, which in turn includes a urethral catheter tube provided with a first urethral catheterization passage, and a branch tube provided with a first passage adapted to allow passage of a fluid used to inflate or deflate a balloon; and a connecting tube configured to be connected at one end to the first urethral catheterization passage or the first passage.

In the aspect of the unit for a balloon catheter according to the present invention, the unit for a balloon catheter further comprises a joint, which in turn includes an insertion port used to insert the balloon catheter and a second urethral catheterization passage and a second passage communicated with the insertion port, wherein the connecting tube is connected at another end to the second urethral catheterization passage or the second passage.

In the aspect of the unit for a balloon catheter according to the present invention, the balloon catheter duct includes a funnel portion forming a space in which the first urethral catheterization passage and the first passage merge together; the joint is configured to be fitted in the funnel portion; and the connecting tube is configured to separate the first urethral catheterization passage or the first passage from the space.

One aspect of an indwelling urethral balloon catheter according to the present invention comprises: the unit for a balloon catheter; a third urethral catheterization passage in fluid communication with the first urethral catheterization passage; and a third passage in fluid communication with the first passage.

Advantageous Effects of Invention

The present invention enables partial replacement of the indwelling urethral catheter.

DESCRIPTION OF EMBODIMENTS

Figure 1:
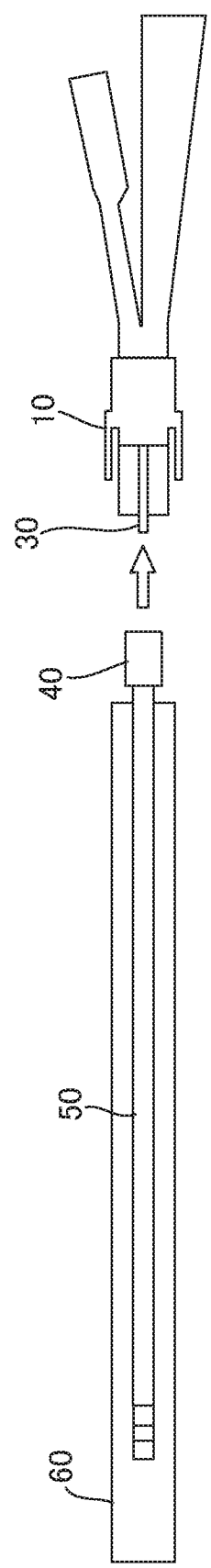
FIG. 1 is an overall schematic diagram of an indwelling urethral balloon catheter according to an embodiment of the present invention.

An embodiment of the present invention will be described below with reference to the drawings. In the drawings described below, same or equivalent components are denoted by the same reference numerals, and redundant description thereof will be omitted.

FIG. 1 is an overall schematic diagram of an indwelling urethral balloon catheter according to the present embodiment. As illustrated in the figure, the indwelling urethral balloon catheter includes a balloon catheter duct 10, a connecting tube 30, a joint 40, a balloon catheter 50, and a case 60. The balloon catheter duct 10 is in fluid communication with the balloon catheter 50 via the joint 40 and connecting tube 30. The joint 40 is a member used to connect the balloon catheter 50 to the balloon catheter duct 10. The case 60 can store an antiseptic solution therein. After use, the balloon catheter 50 is sterilized by being immersed in the antiseptic solution.

The indwelling urethral balloon catheter may be used intermittently by being placed in the urethra only during urination or may be used by being placed in the urethra for a long period of time such as about one month.

According to the present embodiment, the balloon catheter duct 10, connecting tube 30, and joint 40 make up a unit for a balloon catheter. With the indwelling urethral balloon catheter according to the present embodiment, only the balloon catheter 50 is replaced after being used for a predetermined period while the unit for a balloon catheter can be used repeatedly for a long period of time. Alternatively, the balloon catheter 50 and joint 40 may be replaced at the same time, while using the balloon catheter duct 10 and connecting tube 30 repeatedly for a long period of time. The balloon catheter duct 10, connecting tube 30, and joint 40 will be described in detail below.

Figure 2:
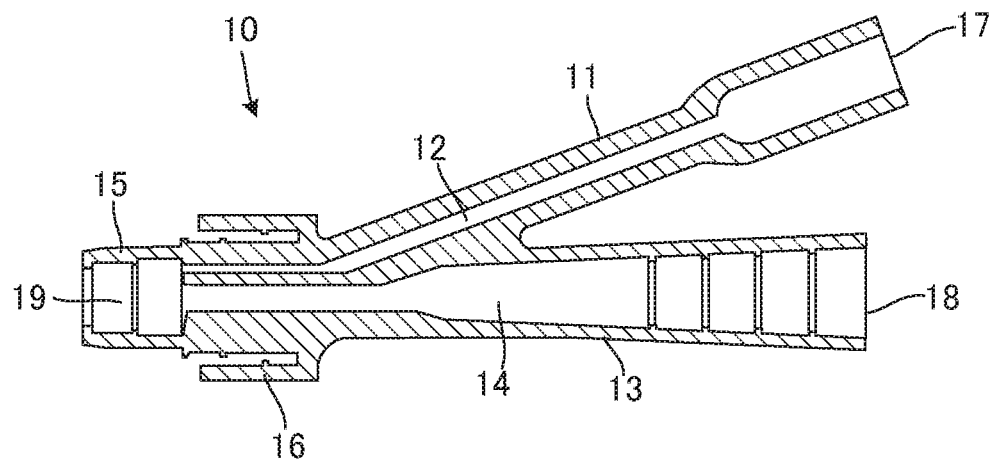
FIG. 2 is a schematic sectional view of a balloon catheter duct according to the present embodiment.

FIG. 2 is a schematic sectional view of the balloon catheter duct 10 according to the present embodiment. The balloon catheter duct 10 includes a urethral catheter tube 13 provided with a first urethral catheterization passage 14, and a branch tube 11 provided with a first passage 12. When the user uses the indwelling urethral balloon catheter, urine passes through the first urethral catheterization passage 14. Also, when a balloon of the balloon catheter 50 inflates or deflates, a fluid such as sterile water or air flows through the first passage 12.

A reservoir connection port 17 for use to connect a reservoir adapted to store sterile water or air is formed at one end of the branch tube 11. A urine drainage port 18 is formed at one end of the urethral catheter tube 13. The urine drainage port 18 can be connected, for example, with a cap for indwelling medical instrument disclosed in Japanese Patent Laid-Open No. 9-206370.

A funnel portion 15 is formed at other ends of the branch tube 11 and urethral catheter tube 13. The funnel portion 15 is a substantially cylindrical member extending from the branch tube 11 and urethral catheter tube 13. The funnel portion 15 forms a space in which the first urethral catheterization passage 14 and first passage 12 merge together. That is, the space 19 which is formed by the funnel portion 15 fluidly communicate with the first urethral catheterization passage 14 and first passage 12.

A fitting portion 16 substantially cylindrical in shape is formed on an outer periphery of the balloon catheter duct 10. An opening of the case 60 shown in FIG. 1 is fitted over the fitting portion 16. In other words, the opening of the case 60 is closed by the fitting portion 16 of the balloon catheter duct 10, inhibiting the antiseptic solution in the case 60 from flowing outside.

Figure 3:
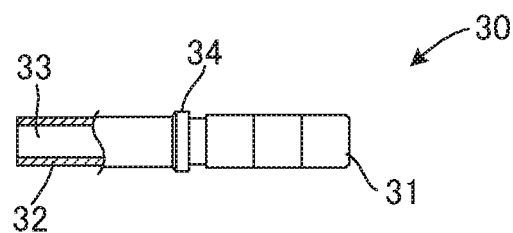
FIG. 3 is a schematic partial sectional view of a connecting tube according to the present embodiment.

FIG. 3 is a schematic partial sectional view of the connecting tube 30 according to the present embodiment. The connecting tube 30 includes a first end portion 31 connected to the first urethral catheterization passage 14 (see FIG. 2) and a second end portion 32 connected to an after-mentioned second urethral catheterization passage 41 (see FIG. 4) of the joint 40. The connecting tube 30 has a flange 34 in a substantially intermediate portion in an axial direction (longitudinal direction). When the connecting tube 30 is inserted into the urethral catheter tube 13 (see FIG. 2), an end portion of the urethral catheter tube 13 abuts the flange 34. This prevents the connecting tube 30 from entering the urethral catheter tube 13 too far.

A duct 33 is formed in the connecting tube 30. When the first end portion 31 of the connecting tube 30 is connected to the first urethral catheterization passage 14 (see FIG. 2) and the second end portion 32 is connected to the second urethral catheterization passage 41 (see FIG. 4), the first urethral catheterization passage 14 fluidly communicates with the second urethral catheterization passage 41 through the duct 33.

Figure 4:
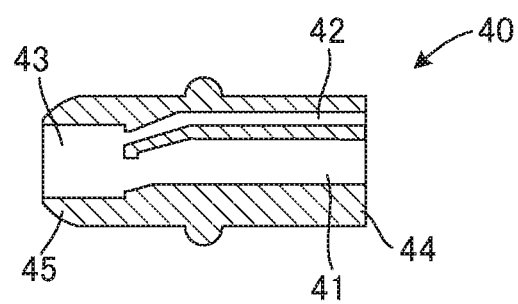
FIG. 4 is a schematic sectional view of a joint according to the present embodiment.

FIG. 4 is a schematic sectional view of a joint according to the present embodiment. The joint 40 is a tubular member, and a first end portion 44 is fitted into the funnel portion 15 (see FIG. 2) of the balloon catheter duct 10. The joint 40 includes an insertion port 43 into which an end portion of the balloon catheter is inserted, and the second urethral catheterization passage 41 and second passage 42 communicated with the insertion port 43. The insertion port 43 is formed on the side of a second end portion 45 and the second urethral catheterization passage 41 and second passage 42 are formed on the side of the first end portion 44. The second urethral catheterization passage 41 is connected with the second end portion 32 of the connecting tube 30 shown in FIG. 3 and fluidly communicates with the duct 33.

The joint 40 is formed, for example, of resin such as plastics and has predetermined rigidity. This makes it easy to fit the first end portion 44 of the joint 40 into the funnel portion 15 of the balloon catheter duct 10.

Figure 5:
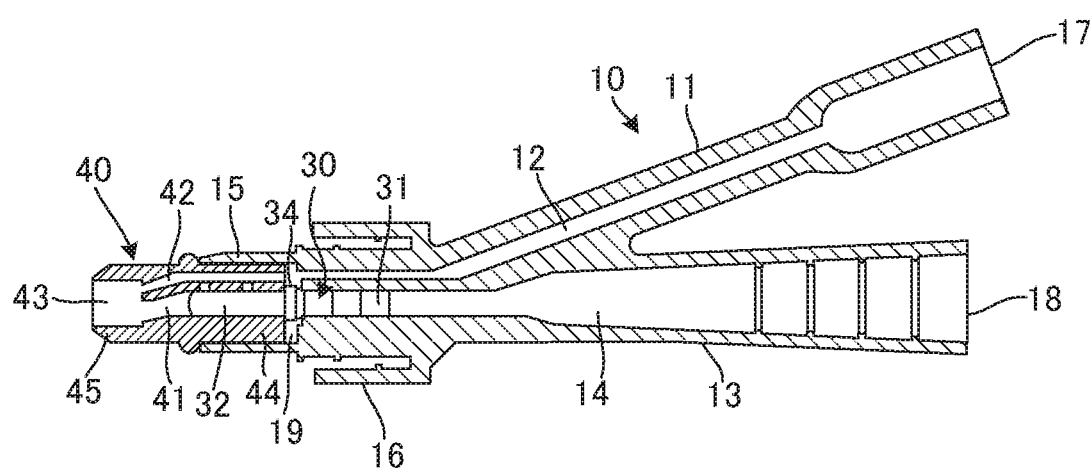
FIG. 5 is a schematic sectional view of a unit for a balloon catheter according to the present embodiment.

FIG. 5 is a schematic sectional view of the unit for a balloon catheter. As shown in FIG. 5, the first end portion 31 of the connecting tube 30 is connected to the first urethral catheterization passage 14 of the balloon catheter duct 10. The second end portion 32 of the connecting tube 30 is connected to the second urethral catheterization passage 41 of the joint 40. The first end portion 44 of the joint 40 is fitted into the funnel portion 15.

As described above, the space 19 in the funnel portion 15 is in fluid communication with the first urethral catheterization passage 14 and first passage 12. However, when the first end portion 31 of the connecting tube 30 is connected to the first urethral catheterization passage 14, the first urethral catheterization passage 14 fluidly communicates with the duct 33 (see FIG. 3) of the connecting tube 30, and no longer communicates with the space 19 in the funnel portion 15. Therefore, by connecting the first end portion 31 to the first urethral catheterization passage 14, the connecting tube 30 can separate the first urethral catheterization passage 14 from the space 19 in the funnel portion 15.

In addition, since the second end portion 32 of the connecting tube 30 is connected to the second urethral catheterization passage 41 of the joint 40, the second urethral catheterization passage 41 is also separated from the space 19 in the funnel portion 15. Therefore, since the first urethral catheterization passage 14 fluidly communicates with the second urethral catheterization passage 41 through the duct 33 (see FIG. 3), a urethral catheterization passage separate from the first passage 12 and second passage 42 is defined.

In a state shown in FIG. 5, the space 19 in the funnel portion 15 fluidly communicates with the first passage 12 and second passage 42. Therefore, via the space 19 in the funnel portion 15, the first passage 12 is communicated with the second passage 42.

Figure 6:
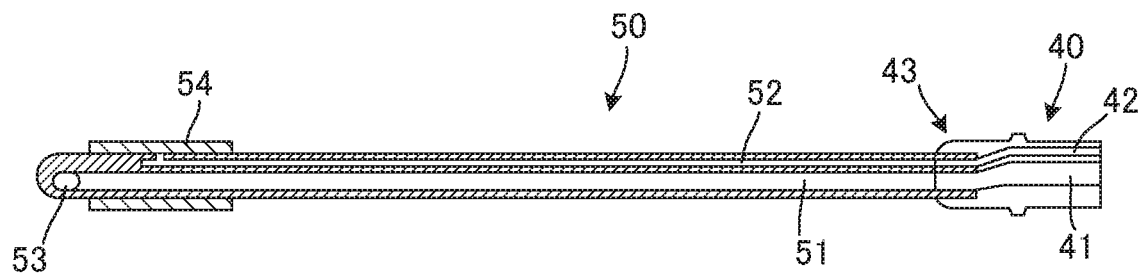
FIG. 6 is a schematic sectional view showing how the joint and balloon catheter are connected together.

FIG. 6 is a schematic sectional view showing how the joint 40 and balloon catheter 50 are connected together. The balloon catheter 50 includes a third urethral catheterization passage 51, a third passage 52, a hole 53 communicated with the third urethral catheterization passage 51, and a balloon 54 communicated with the third passage 52. The hole 53 is formed in a distal end of the balloon catheter 50.

As illustrated in the figure, when one end of the balloon catheter 50 is inserted into the insertion port 43 of the joint 40, the third urethral catheterization passage 51 and third passage 52 fluidly communicate with the second urethral catheterization passage 41 and second passage 42, respectively. Therefore, the third urethral catheterization passage 51 fluidly communicates with the first urethral catheterization passage 14 shown in FIG. 2 via the second urethral catheterization passage 41. Similarly, the third passage 52 fluidly communicates with the first passage 12 shown in FIG. 2 via the second passage 42.

When the balloon catheter 50 is inserted into the urethra of the user, the hole 53 is communicated with the bladder of the user. The urine in the bladder is discharged through the urine drainage port 18 after passing through the hole 53, third urethral catheterization passage 51, second urethral catheterization passage 41, connecting tube 30, and first urethral catheterization passage 14 (see FIGS. 5 and 6).

Also, in placing the balloon catheter 50 in the urethra of the user, sterile water or air is supplied to the balloon 54 from a reservoir connected to the reservoir connection port 17 through the first passage 12, funnel portion 15, second passage 42, and third passage 52 (see FIGS. 5 and 6). Consequently, the balloon 54 is inflated. When the balloon 54 deflates, the sterile water or air returns to the reservoir through a similar route. This allows the balloon catheter 50 to be removed from the urethra of the user.

The balloon catheter 50 may have its surface coated with a hydrophilic material such as a hydrophilic polymer. This makes it easy to insert the balloon catheter 50 into the urethra of the user, and thus possible to inhibit the urethra of the user from being damaged. Thus, urinary tract infection due to damage to the urethra of the user can be prevented.

Also, the balloon catheter 50 may have its surface coated with a photocatalytic material such as titanium dioxide. In that case, the balloon catheter 50 is exposed to ultraviolet rays or visible light, making it possible to disinfect the surface of the catheter.

Also, the balloon catheter 50 may have its surface coated with an antimicrobial material. In that case, the balloon catheter 50 can have antibacterial effects.

Also, the balloon catheter 50 used by being connected to the joint 40 may be a pre-sterilized one. This eliminates the need to sterilize the balloon catheter 50 before use and allows the balloon catheter 50 to be used immediately. Also, if the balloon catheter 50 used is configured to be disposable, the balloon catheter 50 is discarded after being used for a predetermined time. This eliminates the need for a sterilization process, and thus the need for the case 60 shown in FIG. 1.

The hole 53 in the balloon catheter 50 may be formed, for example, in a side face of the balloon catheter 50 or may be formed in a distal end portion such that a drilling direction of the hole 53 will point in a flow path direction of the balloon catheter 50. When the hole 53 is formed in the distal end portion so as to point in the flow path direction of the balloon catheter 50, it is possible to inhibit contamination from building up in the distal end portion of the balloon catheter 50 when cleaning the balloon catheter 50.

When the balloon 54 of the balloon catheter 50 is configured to be inflated or deflated with air rather than sterile water, the balloon 54 may be formed of a material having gas impermeability.

As described above, since the indwelling urethral balloon catheter according to the present embodiment has the connecting tube 30, the balloon catheter 50 can be detachably attached to the balloon catheter duct 10. Therefore, after the indwelling urethral balloon catheter is used multiple times, when it comes time to replace the balloon catheter 50, only the balloon catheter 50 can be replaced. Moreover, running costs involved in self-urethral catheterization of the user can be reduced. Also, if the balloon catheter 50 alone is replaced in a short time, self-urethral catheterization can be done more hygienically.

Also, since the first end portion 31 of the connecting tube 30 is connected to the first urethral catheterization passage 14, when the second end portion 32 fluidly communicates with the balloon catheter 50, the first urethral catheterization passage 14 can fluidly communicate with the balloon catheter 50.

According to the present embodiment, the joint 40 is provided and the second end portion 32 of the connecting tube 30 is connected to the second urethral catheterization passage 41 of the joint 40. This allows the first urethral catheterization passage 14 to fluidly communicate with the second urethral catheterization passage 41 via the connecting tube 30.

According to the present embodiment, as the connecting tube 30 is connected to the first urethral catheterization passage 14, the first urethral catheterization passage 14 is separated from the space 19 in the funnel portion 15. This prevents the urine flowing through the first urethral catheterization passage 14 from being mixed with the sterile water or air flowing through the first passage 12.

According to the present embodiment, the joint 40 is fitted in the funnel portion 15. This allows the first passage 12 to be communicated with the second passage 42 via the space 19 in the funnel portion 15.

Note that although in the present embodiment, the first end portion 31 of the connecting tube 30 is described as being connected to the first urethral catheterization passage 14, the first end portion 31 may be connected to the first passage 12. In that case, the second end portion 32 of the connecting tube 30 will connected to the second passage 42 of the joint 40.

Also, two connecting tubes 30 may be prepared, with the first end portions 31 of the connecting tubes 30 being connected to the first urethral catheterization passage 14 and first passage 12, respectively. In that case, the first urethral catheterization passage 14 and first passage 12 are communicated, respectively, with the second urethral catheterization passage 41 and second passage 42 via the connecting tubes 30, eliminating the need for the funnel portion 15.

Also, although the present embodiment is described as being provided with the joint 40, the second end portion 32 of the connecting tube 30 may be connected directly to the third urethral catheterization passage 51 or third passage 52 of the balloon catheter 50 without the joint 40. In that case, an end portion of the balloon catheter 50 will be fitted directly into the funnel portion 15.

Also, although in the present embodiment, the funnel portion 15 is provided on the balloon catheter duct 10, the funnel portion 15 may alternatively be provided on the joint 40. In that case, the balloon catheter duct 10 will be fitted into the funnel portion 15 of the joint 40.

An embodiment of the present invention has been described above, but the embodiment described above is intended to facilitate understanding of the present invention and is not meant to limit the present invention. The present invention can be modified and improved without departing from the spirit and scope of the present invention. Needless to say, the present invention includes equivalents thereof. Also, the components described in the appended claims and in the specification may be used in any combination or any of the components may be omitted as long as at least some of the problems described above can be solved or as long as at least some of the advantageous effects described above can be achieved.

REFERENCE SIGNS LIST

11 . . . Branch tube
12 . . . First passage
13 . . . Catheter tube
14 . . . First urethral catheterization passage
15 . . . Funnel portion
19 . . . Space
30 . . . Connecting tube
31 . . . First end portion
32 . . . Second end portion
40 . . . Joint
41 . . . Second urethral catheterization passage
42 . . . Second passage
43 . . . Insertion port
50 . . . Balloon catheter
51 . . . Third urethral catheterization passage
52 . . . Third passage
54 . . . Balloon

The invention claimed is:

1. A unit for a balloon catheter comprising:
a balloon catheter duct, which in turn includes a urethra catheter tube provided with a first urethral catheterization passage, and a branch tube provided with a first passage adapted to allow passage of a fluid used to inflate or deflate a balloon;
a joint including an insertion port used to insert the balloon catheter, a second urethral catheterization passage, and a second passage, with each of the insertion port, the second urethral catheterization passage, and the second passage being formed inside the joint; and
a connecting tube configured to be connected at one end to the first urethral catheterization passage or the first passage of the balloon catheter duct, and connected at another end to the second urethral catheterization passage or the second passage of the joint;
wherein the second urethral catheterization passage formed inside the joint and the second passage formed inside the joint each independently communicate with the insertion port formed inside the joint.

2. The unit for a balloon catheter according to claim 1, wherein:
the balloon catheter duct includes a funnel portion forming a space in which the first urethral catheterization passage and the first passage merge together;
the joint is configured to be fitted in the funnel portion; and
the connecting tube is configured to separate the first urethral catheterization passage or the first passage from the space.

3. An indwelling urethral balloon catheter comprising:
the unit for a balloon catheter according to claim 1; and
the balloon catheter, which in turn includes a third urethral catheterization passage in fluid communication with the first urethral catheterization passage and a third passage in fluid communication with the first passage.

4. An indwelling urethral balloon catheter comprising:
the unit for a balloon catheter according to claim 2; and
the balloon catheter, which in turn includes a third urethral catheterization passage in fluid communication with the first urethral catheterization passage and a third passage in fluid communication with the first passage.

5. The unit for a balloon catheter according to claim 1, wherein
the connecting tube is removably connected at the one end to the first urethral catheterization passage or the first passage.

6. The unit for a balloon catheter according to claim 1, wherein
each of the balloon catheter duct, the joint, and the connecting tube are separate components that are removably connected together.

* * * * *